United States Patent
Yuan et al.

[11] Patent Number: 5,932,734
[45] Date of Patent: Aug. 3, 1999

[54] N-AMINOALKYLFLUORENECARBOX-AMIDES

[75] Inventors: Jun Yuan, Clinton; Xi Chen, New Haven, both of Conn.

[73] Assignee: Neurogen Corporation, Branford, Conn.

[21] Appl. No.: 08/908,361

[22] Filed: Aug. 7, 1997

Related U.S. Application Data

[63] Continuation of application No. 08/527,790, Sep. 13, 1995, Pat. No. 5,659,033.

[51] Int. Cl.⁶ .................. C07D 295/15; C07D 211/70
[52] U.S. Cl. .................. 546/203; 546/204; 546/285; 546/281.1; 546/284.1; 546/144; 546/146; 546/265
[58] Field of Search .................. 546/203, 204, 546/285, 144, 146, 265, 281.1, 284.1

[56] References Cited

U.S. PATENT DOCUMENTS

| | | | |
|---|---|---|---|
| 2,527,798 | 10/1950 | Cusic | 546/203 |
| 4,658,061 | 4/1987 | Lacefield et al. | 546/203 |
| 5,395,835 | 3/1995 | Glase et al. | 514/254 |

FOREIGN PATENT DOCUMENTS

| | | |
|---|---|---|
| 0 372 657 A1 | 6/1990 | European Pat. Off. |
| 0 539 281 A1 | 4/1993 | European Pat. Off. |
| 1 537 901 | 8/1968 | France |
| 2 051 556 | 4/1971 | France |
| 2 081 559 | 12/1971 | France |
| WO 95/00131 | 1/1995 | WIPO |
| WO 95/04049 | 2/1995 | WIPO |

*Primary Examiner*—Emily Bernhardt
*Attorney, Agent, or Firm*—McDonnell, Boehnen Hulbert & Berghoff

[57] ABSTRACT

Disclosed are compounds of the formula

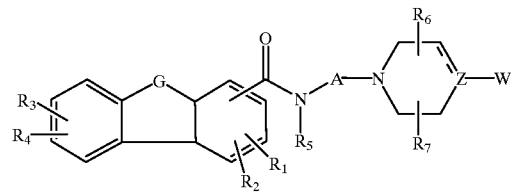

or the pharmaceutically acceptable salts thereof wherein:

G represents a group of the formula

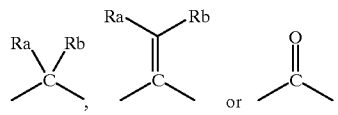

where $R_a$ and $R_b$ represent hydrogen, or organic or inorganic substituents;

A is an optionally substituted alkylene;

$R_1$, $R_2$, $R_3$, $R_4$ represent organic or inorganic substituents;

$R_5$ is hydrogen or lower alkyl;

$R_6$ and $R_7$ independently represent hydrogen, lower alkyl; or together form a ring of 5–8 members;

Z is nitrogen or carbon; and

W is optionally substituted aryl or heteroaryl. Compounds of the present invention demonstrate high affinity and selectivity in binding to the $D_3$ receptor subtype.

9 Claims, No Drawings

N-AMINOALKYLFLUORENECARBOX-AMIDES

This is a continuation of application Ser. No. 08/527,790 filed Sep. 13, 1995, now U.S. Pat. No. 5,659,033.

BACKGROUND OF THE INVENTION

1. Field of the Invention

This invention relates to certain N-alkylaminofluorenecarboxamides and pharmaceutical compositions containing them. It also relates to the use of such compounds in the treatment or prevention of psychotic disorders such as schizophrenia and other central nervous system diseases. The use of the compounds of this invention to the treatment of these disorders is indicated by the ability of the compounds to bind selectively to dopamnine receptor subtypes.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_3$ receptor subtype has recently been identified (Sokoloff, P. et al., *Nature* 1990, 347, 146). Its unique localization in limbic brain areas and its differential recognition of various antipsychotics suggest that the $D_3$ receptor may play a major role in the etiology of schizophrenia. Selective $D_3$ antagonists may be effective antipsychotics free from the neurological side effects displayed by conventional neuroleptics. Compounds of the present invention demonstrate high affinity and selectivity in binding to the $D_3$ receptor subtype. They may be of potential use in treatment of schizophrenia, psychotic depression and mania. Other dopamine-mediated diseases such as Parkinsonism and tardive dyskinesias may also be treated directly or indirectly by modulation of $D_3$ receptors.

Furthermore, compounds of this invention may be useful in treatment of depression, memory-impairment or Alzheimer's disease by modulation of $D_3$ receptors which selectively exist in limbic area known to control emotion and cognitive functions. The compounds of the present invention are also useful for the treatment of other disorders which respond to dopaminergic blockade such as substance abuse (Caine, S. B. and Koob, G. F.; Modulation of Cocaine Self Administration in the Rat through D-3 Dopamine Receptors. *Science* 1993, 260, 1814) and obsessive compulsive disorder (Goodman, W. K. et al., The Role of Serotonin and Dopamine in the Pathophysiology of Obsessive Compulsive Disorder. *Clin. Psychopharmacol.* 1992, 7, 35). The interaction of N-alkylaminofluorenecarboxamides with dopamine receptor subtypes is described. This interaction results in the pharmacological activities of these compounds.

U.S. Pat. No. 5,395,835 May 24, 1994 discloses N-aminoalkyl-2-napthamides which have affinity at dopamine $D_3$ receptors. The novel compounds of claim 1 of the present invention differ significantly from this prior art in that they possess a fluorenecarboxamide substructure.

Murray, P. J. et al. (A Novel Series of Arylpiperazines with High Affinity and Selectivity for the Dopamine $D_3$ Receptor. *Bioorg. Med. Chem. Let.* 1995, 5, 219) described 4-carboxamidobiphenyls which have affinity at dopamine $D_3$ receptors. The novel compounds of the present invention differ significantly from this prior art in that the two aromatic rings of the aromatic carboxamide are fused at the ortho position to create a tricyclic ring system.

SUMMARY OF THE INVENTION

This invention provides novel compounds of Formula I which interact with dopamine receptor subtypes. Thus, the invention provides compounds of general Formula I useful in the treatment and/or prevention of various neuropsychological disorders. The invention also provides pharmaceutical compositions comprising compounds of Formula 1.

The invention further relates to the use of such compounds in the treatment of affective disorders such as schizophrenia, depression, Alzheimer's disease and certain movement disorders such as Parkinsonism and dystonia. Furthermore compounds of this invention are useful in treating the extrapyramidal side effects associated with the use of conventional neuroleptic agents. The compounds of the present invention are also useful for the treatment of other disorders which respond to dopaminergic blockade such as substance abuse and obsessive compulsive disorder. Since dopamine $D_3$ receptors are concentrated in the limbic system (Taubes, *Science* 265 (1994) 1034) which controls cognition and emotion, compounds which interact with these receptors have utility in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention that interact specifically with the dopamine $D_3$ receptor subtype.

Accordingly, a broad embodiment of the invention is directed to a compound of Formula I:

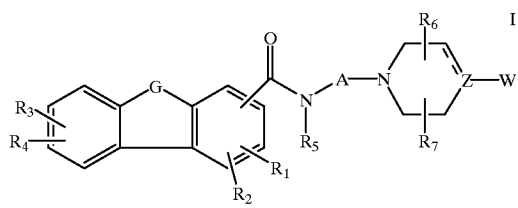

or the pharmaceutically acceptable salts thereof wherein:
G represents a group of the formula

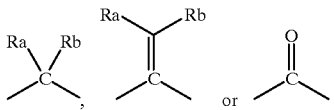

where $R_a$ and $R_b$ independently represent hydrogen, $C_1-C_6$ alkyl, hydroxy, $C_1-C_6$ alkoxy or mono- or di-$C_1-C_6$ alkylamino;

A is a $C_2-C_6$ alkylene optionally substituted with one or more alkyl groups having from one to four carbon atoms;

$R_1$, $R_2$, $R_3$, $R_4$ are the same or different and represent hydrogen, $C_1-C_6$ alkyl, halogen, hydroxy, amino, cyano, nitro, trifluoromethyl, trifluoromethoxy, $C_1-C_6$ alkoxy, —$O_2CR'$, —NHCOR', —COR', —$SO_mR'$, where R' is $C_1-C_6$ alkyl and wherein m is 0, 1 or 2; or $R_1$, $R_2$, $R_3$, $R_4$ independently represent —CONR'$_m$, or —NR'$_m$ where m is 0, 1 or 2 and R' is hydrogen or $C_1-C_6$ alkyl;

$R_5$ is hydrogen or $C_1-C_6$ alkyl;

$R_6$ and $R_7$ are the same or different and are hydrogen or $C_1-C_6$ alkyl; or $R_6$ and $R_7$ together form a ring having 5–8 atoms;

Z is N or C; and

W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Thus the invention relates to the use of compounds of formula I in the treatment and/or prevention of neuropsychochological disorders including, but not limited to, schizophrenia, mania, dementia, depression, anxiety, compulsive behavior, substance abuse, memory impairment, cognitive deficits, Parkinson-like motor disorders and motion disorders related to the use of neuroleptic agents.

DETAILED DESCRIPTION OF THE INVENTION

The novel compounds encompassed by the invention can be described by general formula

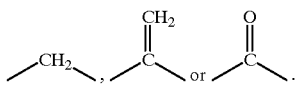
I or the pharmaceutically acceptable salts thereof wherein:

G represents a group of the formula

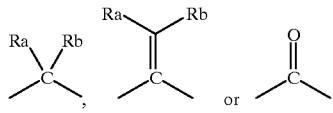

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms;

Z is N or C; and

W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula I are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula I are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

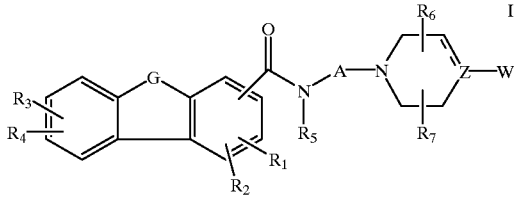

Particularly preferred compounds of formula I are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

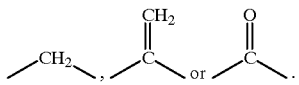

Still more preferred compounds of formula I are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

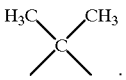

The present invention further encompasses compounds of Formula II:

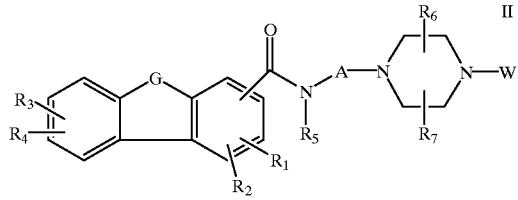
II or the pharmaceutically acceptable acid addition salts thereof; wherein:

G represents a group of the formula

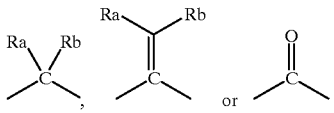

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula II are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula II are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

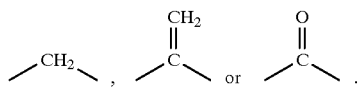

Particularly preferred compounds of formula II are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

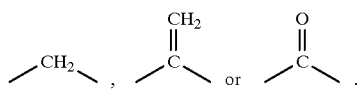

The present invention further encompasses compounds of Formula III:

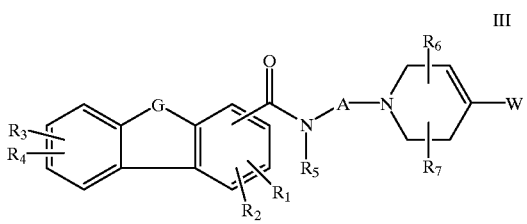

III or the pharmaceutically acceptable acid addition salts thereof; wherein:

G represents a group of the formula

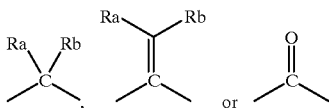

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula III are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula III are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

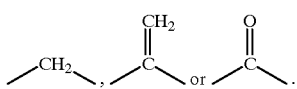

Particularly preferred compounds of formula III are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

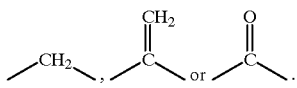

The present invention also encompasses compounds of Formula IV:

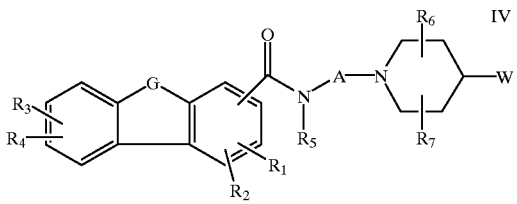

or the pharmaceutically acceptable acid addition salts thereof; wherein:

G represents a group of the formula

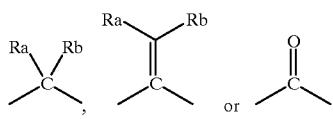

where $R_a$ and $R_b$ independently represent hydrogen, $C_1-C_6$ alkyl, hydroxy, $C_1-C_6$ alkoxy or mono- or di-$C_1-C_6$ alkylamino;

A is a $C_2-C_6$ alkylene optionally substituted with one or more alkyl groups having from one to four carbon atoms;

$R_1$, $R_2$, $R_3$, $R_4$ are the same or different and represent hydrogen, $C_1-C_6$ alkyl, halogen, hydroxy, amino, cyano, nitro, trifluoromethyl, trifluoromethoxy, $C_1-C_6$ alkoxy, —$O_2CR'$, —NHCOR', —COR', —$SO_mR'$, where R' is $C_1-C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1-C_6$ alkyl;

$R_5$ is hydrogen or $C_1-C_6$ alkyl;

$R_6$ and $R_7$ are the same or different and are hydrogen or $C_1-C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1-C_6$ alkyl, $C_1-C_4$ alkoxy, thioalkoxy, hydroxy, amino, mono or dialkylamino where each alkyl is $C_1-C_6$ alkyl, cyano, nitro, trifluoromethyl or trifluoromethoxy.

Preferred compounds of formula IV are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula IV are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

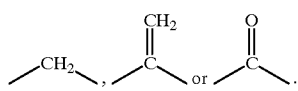

Particularly preferred compounds of formula IV are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

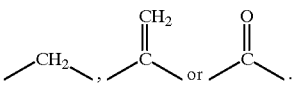

The present invention also encompasses compounds of Formula V:

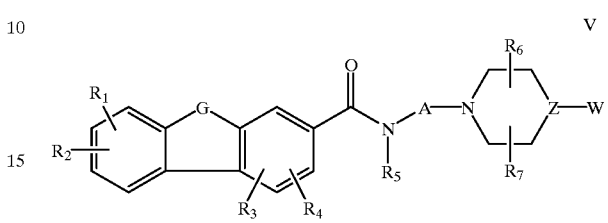

or the pharmaceutically acceptable acid addition salts thereof; wherein:

G represents a group of the formula

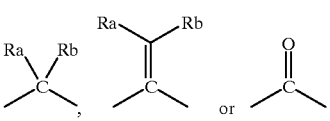

where $R_a$ and $R_b$ independently represent hydrogen, $C_1-C_6$ alkyl, hydroxy, $C_1-C_6$ alkoxy or mono- or di-$C_1-C_6$ alkylamino;

A is a $C_2-C_6$ alkylene optionally substituted with one or more alkyl groups having from one to four carbon atoms;

$R_5$ is hydrogen or $C_1-C_6$ alkyl;

$R_6$ and $R_7$ are the same or different and are hydrogen or $C_1-C_6$ alkyl; or $R_6$ and $R_7$ together form a ring having 5–8 atoms; and W is phenyl, naphthyl, 1-(5,6,7,8-tetrahydro)naphthyl or 4(1,2-dihydro)indenyl, pyridinyl, pyrimidyl, isoquinolinyl, benzofuranyl, benzothienyl, each of which is optionally substitutedwith up to three groups selected from the following: halogen, $C_1-C_6$ alkyl, $C_1-C_4$ alkoxy, thioalkoxy, hydroxy, amino, mono or dialkylamino where each alkyl is $C_1-C_6$ alkyl, cyano, nitro, trifluoromethyl or trifluoromethoxy.

Preferred compounds of formula V are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula V are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

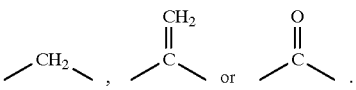

Particularly preferred compounds of formula V are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

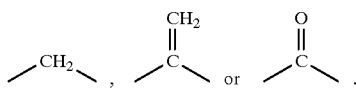

The present invention also encompasses compounds of Formula VI:

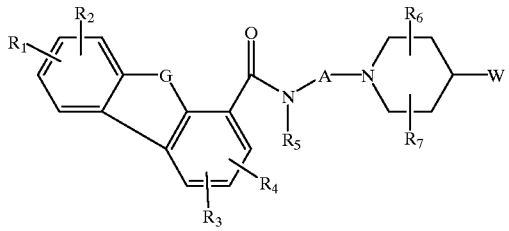

VI or the pharmaceutically acceptable acid addition salts thereof; wherein:

G represents a group of the formula

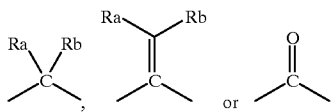

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substitutedwith up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula VI are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula VI are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

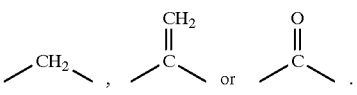

Particularly preferred compounds of formula VI are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

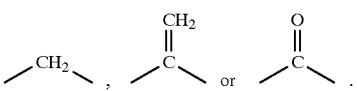

The present invention also encompasses compounds of Formula VII:

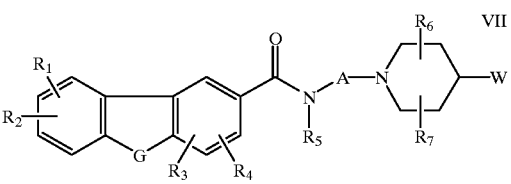

VII or the pharmaceutically acceptable acid addition salts thereof; wherein:

G represents a group of the formula

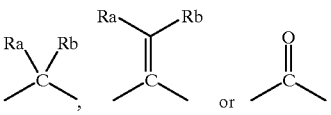

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms; $R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substitutedwith up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula VII are those where $R_1$, $R_2$, $R_3$, $R_4$ are hydrogen, $R_5$ is hydrogen, methyl, or ethyl;

A is an optionally substituted ethylene, propylene, or butylene group; and $R_6$ and $R_7$ are hydrogen. More preferred compounds of formula VII are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

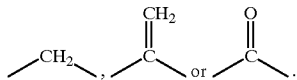

Particularly preferred compounds of formula VII are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

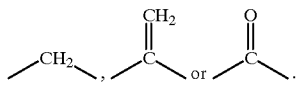

The present invention also encompasses compounds of Formula VIII:

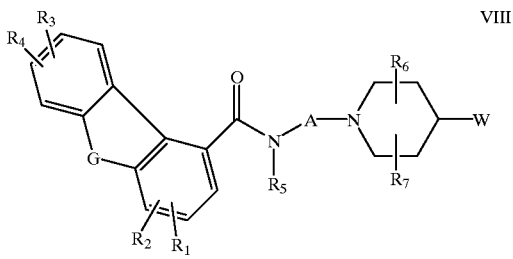

or the pharmaceutically acceptable acid addition salts thereof; wherein:

G represents a group of the formula

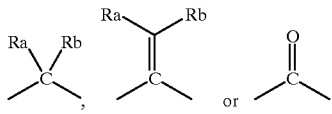

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —CONR'$_m$, or —NR'$_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula VIII are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula VIII are those where $R_1$, $R_2$, $_3$, $R_4$ are hydrogen, $R_5$ is hydrogen, methyl, or ethyl; A is an optionally substituted ethylene, propylene, or butylene group; $R_6$ and $R_7$ are hydrogen; and G is

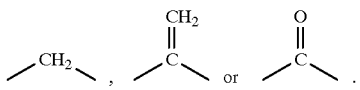

Particularly preferred compounds of formula VIII are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

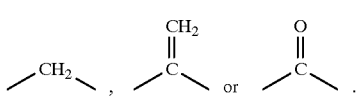

The present invention also encompasses compounds of Formula IX:

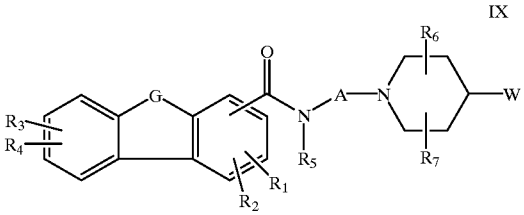

or the pharmaceutically acceptable acid addition salts thereof; wherein:

G represents a group of the formula

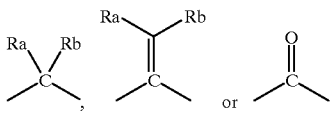

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —CONR'$_m$, or —NR'$_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; or $R_6$ and $R_7$ together form a ring having 5–8 atoms; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, thioalkoxy, hydroxy, amino, mono or dialkylamino where each alkyl is $C_1$–$C_6$ alkyl, cyano, nitro, trifluoromethyl or trifluoromethoxy.

Preferred compounds of formula IX are those where $R_1$, $R_2$, $R_3$, $R_4$ are hydrogen, $R_5$ is hydrogen, methyl, or ethyl; A is an optionally substituted ethylene, propylene, or butylene group; and $R_6$ and $R_7$ are hydrogen. More preferred compounds of formula IX are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; and G is

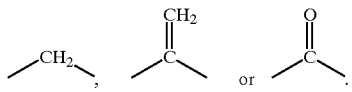

Particularly preferred compounds of formula IX are those where $R_1$, $R_2$, $R_3$, $R_4$ are hydrogen, $R_5$ is hydrogen, methyl, or ethyl; A is an optionally substituted ethylene, propylene, or butylene group; $R_6$ and $R_7$ are hydrogen; Z is nitrogen and G is

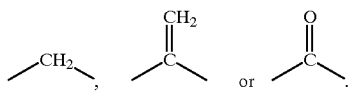

When a compound of formula I is obtained as a mixture of enantiomers, these enantiomers may be separated, when desired, by conventional methods such as crystallization in the presence of a resolving agent, or chromatography, for example using a chiral HPLC column.

Representative compounds of the present invention, which are encompassed by Formula I, include, but are not limited to the compounds in FIG. I and their pharmaceutically acceptable salts. The present invention also encompasses prodrugs of the compounds of Formula I. Those skilled in the art will recognize various synthetic methodologies which may be employed to prepare non-toxic pharmaceutically acceptable addition salts and prodrugs of the compounds encompassed by Formula I.

Representative compounds of the present invention, which are encompassed by Formula 1, include, but are not limited to the compounds shown below in Table 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula 1. Those skilled in the art will recognize various synthetic methodologies which can be employed to prepare non-toxic pharmaceutically acceptable addition salts and acylated prodrugs of the compounds encompassed by Formula 1.

By "alkyl" and "lower alkyl" is meant straight and branched chain alkyl groups having from 1–6 carbon atoms, e.g., $C_1$–$C_6$ alkyl.

By "lower alkoxy" and "alkoxy" is meant straight and branched chain alkoxy groups having from 1–6 carbon atoms, e.g., $C_1$–$C_6$ alkoxy.

By halogen is meant fluorine, chlorine, bromine and iodine.

The group of the formula

where W is defined above designates saturated heterocyclic ring systems such as, for example, piperidinyl and piperazinyl, as well as unsaturated heterocyclic ring systems such as, for example, 1, 2, 3, 6-tetrahydropyrindine.

Preferred groups of this formula are the following:

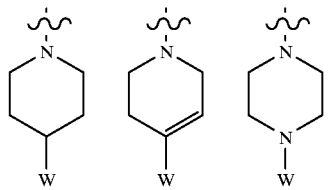

where W is defined above.

By thioalkoxy and alkylthio is meant a group of the formula R'S— where R' is lower alkyl.

Representative examples of N-alkylaminofluorenecarboxamides according to the invention are shown in Table 1 below. The number below each compound is its compound number. Each of these compounds may be prepared by general reaction scheme I set forth below.

TABLE 1

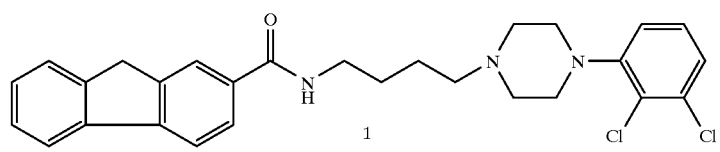

TABLE 1-continued
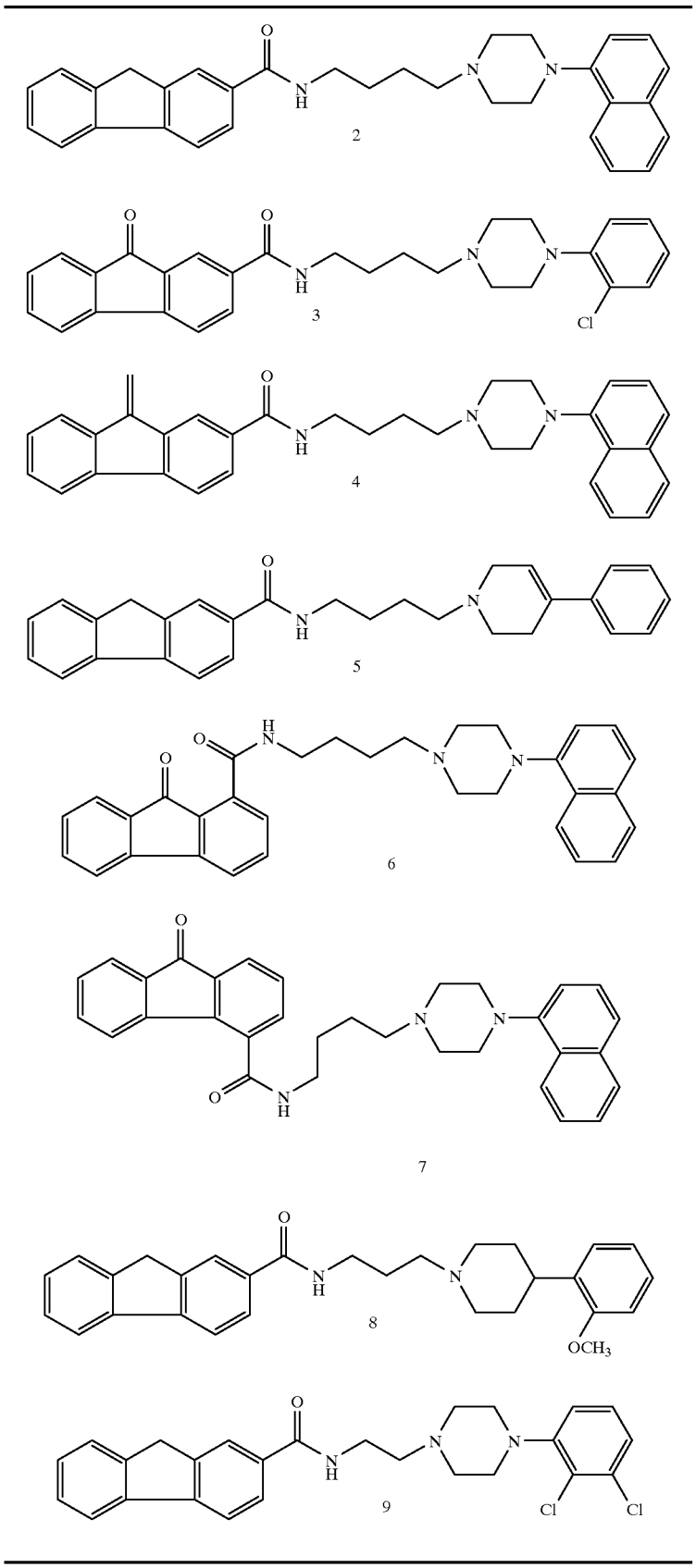

The compounds of the invention are suitable for the treatment and/or prevention of affective disorders such as schizophrenia, depression, Alzheimer's disease and certain movement disorders such as Parkinsonism and dystonia. Furthermore compounds of this invention are useful in treating the extrapyramidal side effects associated with the use of conventional neuroleptic agents. These compounds are also useful in treating other disorders which respond to dopaminergic blockade such as substance abuse and obsessive compulsive disorder.

Dopamine $D_3$ receptors are concentrated in the limbic system (Taubes, *Science* 265 (1994) 1034). This system controls cognition and emotion. Thus, compounds which interact with dopamine $D_3$ receptors can be used in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention that interact specifically with the dopamine $D_3$ receptor subtype.

The compounds of the invention can be used to treat and/or prevent neuropsychological disorders including, for example, schizophrenia, mania, dementia, depression, anxiety, compulsive behavior, substance abuse, Parkinson-like motor disorders and motion disorders related to the use of neuroleptic agents, which comprises administering to a host in need of such treatment an effective amount of a compound as claimed in claim 1.

The pharmaceutical utility of compounds of this invention are indicated by the following assays for dopamine receptor subtype affinity.

Assay for $D_2$ and $D_3$ Receptor Binding Activity

Pellets of COS cells containing recombinantly produced $D_2$ or $D_3$ receptors from African Green monkey were used for the assays. The sample is homogenized in 100 volumes (w/vol) of 0.05M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of examples of this patent for the $D_2$ and $D_3$ receptor subtypes are shown in Table 2 for rat striatal homogenates.

TABLE 2[1]

| Compound Number[1] | $D_2$ $K_i$ (nM) | $D_3$ $K_i$ (nM) |
|---|---|---|
| 1 | 729 | 3 |
| 2 | 150 | 1 |
| 3 | 97 | 0.7 |

[1]Compound numbers relate to compounds shown above in Table 1.

Compounds 1, 2 and 3 are particularly preferred embodiments of the present invention because of their potency in binding to dopamine receptor subtypes.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The N-alkylaminofluorenecarboxamides of the invention may be prepared employing the reactions set forth below in Scheme 1. Those having skill in the art will recognize that the starting materials may be varied and additional steps employed to produce other compounds encompassed by the present invention.

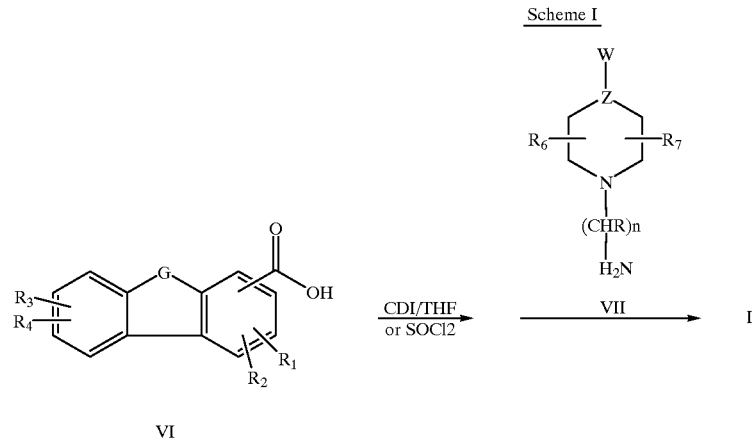

Scheme I

In Scheme I, the substituents $R_1$, $R_2$, $R_3$, $R_4$, $R_5$, $R_6$, $R_7$, G, Z and W are as defined above.

As shown in Scheme I, an acid VI may be activated with a reagent such as, 1,1'-carbonyldiimidazole (CDI) or thionyl chloride ($SOCl_2$), in a solvent such as, for example, tetrahydrofuran or dichloromethane at room temperature. Those skilled in the art will recognize that other suitable activating reagents may be used in place of CDI and $SOCl_2$. Subsequently, the resulting activated carboxylate intermediate typically is reacted with an amine VII to afford a compound of formula I as the desired product.

When not commercially available, the amine VI may be prepared by procedures known to those skilled in the art and described in the pertinent literature. A variety of amines of formula VII are known; others may be prepared by methods known in the art.

The invention is further illustrated by the following examples which are not to be construed as limiting the invention in scope or spirit to the specific procedures and compounds described therein.

EXAMPLE 1
N-{4-[4-(2,3-dichlorophenyl)-1-piperazinyl]butyl}-9H-fluorene-2-carboxamide hydrochloride (Table 1, Compound 1)

A mixture of 9H-fluorene-2-carboxylic acid (100 mg, 0.48 mmol) and 1,1'-carbonyldiimidazole (80 mg, 0.5 mmol) in 10 mL of anhydrous tetrahydrofuran was stirred for 8 hours. A solution of 4-[4-(2,3-dichlorophenyl)-1-piperazinyl]-1-aminobutane (150 mg, 0.5 mmol) in 1 mL of tetrahydrofuran was added and the resulting mixture was stirred for 30 minutes. The reaction mixture was partitioned between ethyl acetate and water. The organic layer was washed with aqueous $Na_2CO_3$ solution, dried ($Na_2SO_4$) and concentrated in vacuo to give the title compound (185mg, 78%). Hydrochloride salt was prepared by treating the free base with a solution of hydrogen chloride in ethyl acetate (mp 262–4° C.).

The following compounds of are prepared essentially according to the procedures set forth in Example 1 for the preparation of Compound 1.

EXAMPLE 2
N-{4-[4-(2,3-Dichlorophenyl)-1-piperazinyl]butyl}-9-oxo-fluorene-2-carboxamide hydrochloride (mp 229–231° C.).

EXAMPLE 3
N-{4-[4-(1-Naphthyl)-1-piperazinyl]butyl}-9H-fluorene-2-carboxamide hydrochloride (Compound 2, mp 240–242° C.).

EXAMPLE 4
N-{4-[4-(1-Naphthyl)-1-piperazinyl]butyl}-9-oxo-fluorene-2-carboxamide hydrochloride (mp 207–210° C.).

EXAMPLE 5
N-{4- [4-(2,3-Dimethylphenyl)-1-piperazinyl]butyl}-9H-fluorene-2-carboxamide hydrochloride (mp 266–267° C.).

EXAMPLE 6
N-{4-[4-(2,3-Dimethylphenyl)-1-piperazinyl]butyl}-9-oxo-fluorene-2-carboxamide hydrochloride (mp 250–252° C.).

EXAMPLE 7
N-{4-[4(2-Methylphenyl)-1-piperazinyl]butyl}-9H-fluorene-2carboxamide dihydrochloride (mp 235–237° C.).

EXAMPLE 8
N-{4-[4(2,6-Dimethylphenyl)-1-piperazinyl]butyl}-9H-fluorene-2-carboxamide hydrochloride (mp 246–249° C.).

EXAMPLE 9
N-{4-[4-(2-Chlorophenyl)-1-piperazinyl]butyl}-9H-fluorene-2-carboxamide hydrochloride (mp 255–257° C.).

EXAMPLE 10
N-{4-[4-(2-Chlorophenyl)-1-piperazinyl]butyl}-9-oxo-fluorene-2-carboxamide hydrochloride (Compound 3, mp 217–218° C.).

EXAMPLE 11
N-{4-[4-(2-Methoxyphenyl)-1-piperazinyl]butyl}-9H-fluorene-2-carboxamide hydrochloride (mp 260–263° C.).

EXAMPLE 12
N-{4-[4-(2-Methoxyphenyl)-1-piperazinyl]butyl}-9-oxo-fluorene-2-carboxamide hydrochloride (mp 250–252° C.).

EXAMPLE 13
N-{4-[4-(1-Naphthyl)-1-piperazinyl]butyl}-9-methylene-fluorene-2-carboxamide hydrochloride (Compound 4, mp 252–254° C.).

EXAMPLE 14
(±)N-{4-[4-(2,3-Dichlorophenyl)-1-piperazinyl]butyl}-9-methyl-9H-fluorene-2-carboxamide hydrochloride (mp 238–240° C.).

EXAMPLE 15
N-{4-[4-(2,3-dichlorophenyl)-1-piperazinyl]butyl}-9H-fluorene-1-carboxamide hydrochloride (mp 189–191° C.).

EXAMPLE 16
N-{4-[4-(1-Naphthyl)-1-piperazinyl]butyl}-9-oxo-fluorene-1-carboxamide hydrochloride (Compound 6, mp 157–160° C.).

EXAMPLE 17
N-{4-[4-(1-Naphthyl)-1-piperazinyl]butyl}-9-oxo-fluorene-4-carboxamide hydrochloride (Compound 7, mp 194–196° C.).

EXAMPLE 18
N-{4-[4-(2-Methoxyphenyl)-1-piperazinyl]propyl}-9H-fluorene-2-carboxamide hydrochloride (Compound 8, mp 210–212° C.).

EXAMPLE 19
N-{4-[4-(2,3-Dichlorophenyl)-1-piperazinyl]ethyl} -9H-fluorene-2-carboxamide hydrochloride (Compound 9, mp 233–236° C.).

EXAMPLE 20
N-{4-[4-(8-Isoquinolinyl)-1-piperazinyl]butyl}-9H-fluorene-2-carboxamide hydrochloride (mp 192–195° C.).

EXAMPLE 21
N-{4-[4-Phenyl-1-(1,2,3,6-tetrahydropyridyl)]butyl}-9H-fluorene-2-carboxamide hydrochloride (Compound 5, mp 265–267° C.).

EXAMPLE 22
N-{4-[4-(3-Chloro-2-methylphenyl)-1-piperazinyl]butyl}-9H-fluorene-2-carboxamide hydrochloride (mp 246–247° C.).

EXAMPLE 23
N-[4-(4-Phenyl-1-piperidyl)butyl]-9H-fluorene-2-carboxamide hydrochloride (mp 212–214° C.).

EXAMPLE 24
N-{4-[4-(2,3-Dichlorophenyl)-1-piperazinyl]butyl}-9-dimethyl-9H-fluorene-2-carboxamide hydrochloride (mp 241–3° C.).

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A compound of the formula:

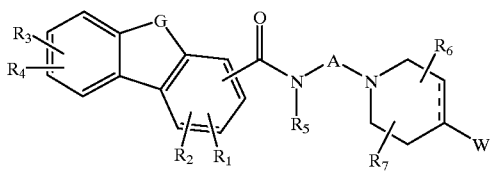

or the pharmaceutically acceptable salts thereof wherein:

G represents a group of the formula

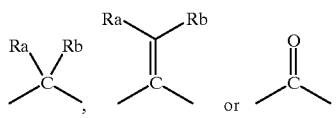

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms; $R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; and W is phenyl, naphthyl, 1-(5,6,7,8-tetrahydro)naphthyl or 4-(1,2-dihydro) indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, $C_1$–$C_6$ thioalkoxy, hydroxy, amino, mono or dialkylamino where each alkyl is $C_1$–$C_6$ alkyl, cyano, nitro, trifluoromethyl or trifluoromethoxy.

2. A compound of the formula:

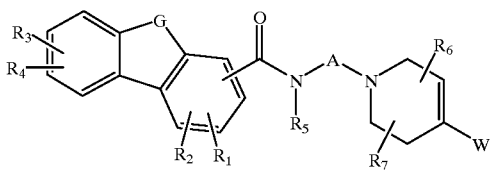

or the pharmaceutically acceptable acid addition salts thereof; wherein:

G represents a group of the formula

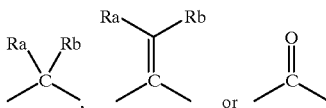

where $R_a$ and $R_b$ independently represent hydrogen, $C_1$–$C_6$ alkyl, hydroxy, $C_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$ $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, $C_1$–$C_6$ thioalkoxy, hydroxy, amino, mono or dialkylamino where each alkyl is $C_1$–$C_6$ alkyl, cyano, nitro, trifluoromethyl or trifluoromethoxy.

3. A compound of the formula:

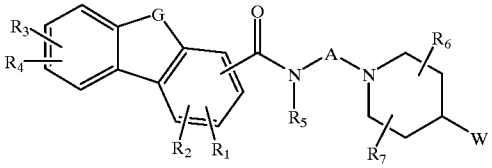

or the pharmaceutically acceptable acid addition salts thereof; wherein:

G represents a group of the formula

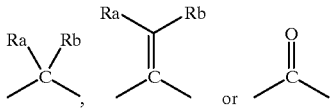

where $R_a$ and $R_b$ independently represent hydrogen, $C_1$–$C_6$ alkyl, hydroxy, $R_1$–$C_6$ alkoxy or mono- or di-$C_1$–$C_6$ alkylamino;

A is a $C_2$–$C_6$ alkylene optionally substituted with one or more alkyl groups having from one to four carbon atoms;

$R_1$, $R_2$, $R_3$, $R_4$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$, $R_2$, $R_3$, $R_4$ independently represent —$CONR'_m$, or —$NR'_m$ where m is 0, 1 or 2 and R' is hydrogen or $C_1$–$C_6$ alkyl;

$R_5$ is hydrogen or $C_1$–$C_6$ alkyl;

$R_6$ and $R_7$ are the same or different and are hydrogen or $C_1$–$C_6$ alkyl; and W is phenyl, naphthyl, 1-(5,6,7,8-tetrahydro)naphthyl or 4-(1,2-dihydro)indenyl, pyridinyl, pyrimidyl, isoquinolinyl, benzofuranyl, benzothienyl, each of which is optionally substituted with up to three groups selected from the following: halogen, $C_1$–$C_6$ alkyl, $C_1$–$C_4$ alkoxy, $C_1$–$C_6$ thioalkoxy, hydroxy, amino, mono or dialkylamino where each alkyl is $C_1$–$C_6$ alkyl, cyano, nitro, trifluoromethyl or trifluoromethoxy.

4. A compound according to claim 2, which is N-{4-[4-Phenyl-1-(1,2,3,6-tetrahydropyridly)]butyl}-9H-fluorene-2-carboxamide hydrochloride.

5. A compound according to claim 3, which is N-[4-(4-Phenyl-1-piperidyl)butyl]-9H-fluorene-2-carboxamide hydrochloride.

6. A compound according to claim 3, wherein $R_1$, $R_2$, $R_3$, and $R_4$ are hydrogen; $R_a$ and $R_b$ represent hydrogen; and A is a ethylene, propylene or butylene.

7. A compound according to claim 2, wherein $R_1$, $R_2$, $R_3$, and $R_4$ are hydrogen; $R_a$ and $R_b$ represent hydrogen; and A is a ethylene, propylene or butylene.

8. A compound according to claim 6, wherein $R_5$ is hydrogen and W is phenyl or naphthyl, each of which is optionally substituted with one or two groups selected from halogen, $C_{1-C6}$ alkyl, $C_1$–$C_4$ alkoxy, $C_1$–$C_4$ thioalkoxy, hydroxy, amino, mono or di-$C_1$–$C_6$ alkylamino where each alkyl is $C_1$–$C_6$ alkyl, cyano, nitro, trifluoromethyl or trifluoromethoxy.

9. A compound according to claim 7, wherein $R_5$ is hydrogen and W is phenyl or naphthyl, each of which is optionally substituted with one or two groups selected from halogen, $C_1$–$C_6$ alkyl, $C_1$–$C_4$ alkoxy, $C_{1-C4}$ thioalkoxy, hydroxy, amino, mono or di-$C_1$–$C_6$ alkylamino where each alkyl is $C_1$–$C_6$ alkyl, cyano, nitro, trifluoromethyl or trifluoromethoxy.

\* \* \* \* \*